(12) United States Patent
Jung et al.

(10) Patent No.: US 11,658,749 B2
(45) Date of Patent: May 23, 2023

(54) SENSOR DEVICE AND MOBILE DEVICE INCLUDING THE SAME

(71) Applicant: SAMSUNG ELECTRONICS CO., LTD., Suwon-si (KR)

(72) Inventors: Sungjin Jung, Hwaseong-si (KR); Long Yan, Hwaseong-si (KR); Seoungjae Yoo, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 43 days.

(21) Appl. No.: 17/494,118

(22) Filed: Oct. 5, 2021

(65) Prior Publication Data

US 2022/0247497 A1 Aug. 4, 2022

(30) Foreign Application Priority Data

Feb. 3, 2021 (KR) ........................ 10-2021-0015316

(51) Int. Cl.
*A61B 5/024* (2006.01)
*H04B 10/556* (2013.01)
*H04B 10/54* (2013.01)
*A61B 5/026* (2006.01)
*H04B 10/516* (2013.01)

(52) U.S. Cl.
CPC ......... *H04B 10/556* (2013.01); *A61B 5/0261* (2013.01); *A61B 5/02427* (2013.01); *H04B 10/5161* (2013.01); *H04B 10/541* (2013.01)

(58) Field of Classification Search
None
See application file for complete search history.

(56) References Cited

U.S. PATENT DOCUMENTS

| | | | | |
|---|---|---|---|---|
| 5,987,343 A * | 11/1999 | Kinast | ............... | A61B 5/14551 600/323 |
| 7,268,334 B2 * | 9/2007 | Tsou | ..................... | H04N 5/335 257/443 |
| 9,246,598 B2 * | 1/2016 | Asmanis | ............. | H04B 10/504 |
| 9,743,086 B2 | 8/2017 | Sato | | |
| 9,844,348 B2 * | 12/2017 | Mannheimer | ......... | G01D 18/00 |
| 10,003,407 B2 * | 6/2018 | Perez De Aranda Alonso | ............ | H04L 1/0042 |
| 10,326,634 B2 | 6/2019 | Zhang et al. | | |
| 10,409,048 B2 * | 9/2019 | Cheng | .................. | G01R 31/311 |
| 11,231,779 B1 * | 1/2022 | Sundberg | ............. | G06F 1/1686 |
| 11,291,401 B2 * | 4/2022 | Velo | ...................... | A61B 5/282 |
| 11,330,993 B2 * | 5/2022 | Basu | .................... | A61B 5/1455 |
| 11,369,275 B2 * | 6/2022 | Song | .................. | A61B 5/02416 |
| 11,380,118 B2 * | 7/2022 | Shaker | ................ | G06V 10/143 |
| 11,464,429 B2 * | 10/2022 | Conrad | ................... | A61B 5/05 |
| 2006/0072835 A1 * | 4/2006 | Zhu | ........................ | H04N 19/59 382/232 |

(Continued)

*Primary Examiner* — Jai M Lee
(74) *Attorney, Agent, or Firm* — Lee IP Law, P.C.

(57) ABSTRACT

A sensor device includes a sensor array including a plurality of photodiodes configured to generate current signals in response to light, an encoder configured to encode the current signals to generate a plurality of analog signals and output the plurality of analog signals sequentially, a signal processing module configured to process the analog signals, received from the encoder, to generate digital signals, and a decoder configured to decode the digital signals, received from the signal processing module, to generate a plurality of data signals corresponding to the current signals.

20 Claims, 16 Drawing Sheets

(56) References Cited

U.S. PATENT DOCUMENTS

| | | | |
|---|---|---|---|
| 2012/0143025 A1* | 6/2012 | Porges | A61B 5/14551 |
| | | | 600/323 |
| 2015/0221111 A1* | 8/2015 | Battista, Jr. | G06T 11/206 |
| | | | 345/440.1 |
| 2016/0080102 A1 | 3/2016 | Fang | |
| 2016/0204873 A1 | 7/2016 | Perez De Aranda Alonso et al. | |
| 2016/0256079 A1* | 9/2016 | Shimano | A61B 5/6826 |
| 2021/0100463 A1* | 4/2021 | Gunturi | A61B 5/681 |
| 2021/0353226 A1* | 11/2021 | Hiemstra | G06F 1/181 |
| 2021/0378535 A1* | 12/2021 | Pande | A61B 5/02427 |
| 2022/0007954 A1* | 1/2022 | Korkala | A61B 5/14552 |
| 2022/0104719 A1* | 4/2022 | Galdi | A61B 5/02433 |
| 2022/0296111 A1* | 9/2022 | Leabman | A61B 5/681 |

* cited by examiner $$\begin{array}{c} \phantom{T1} \quad \text{ENC1 ENC2 ENC3 ENC4} \\ \begin{array}{c} T1 \\ T2 \\ T3 \\ T4 \end{array} \begin{bmatrix} +1 & -1 & -1 & -1 \\ -1 & +1 & -1 & -1 \\ -1 & -1 & +1 & -1 \\ -1 & -1 & -1 & +1 \end{bmatrix} \times \begin{bmatrix} I1 \\ I2 \\ I3 \\ I4 \end{bmatrix} = \begin{bmatrix} +I1-I2-I3-I4 \\ -I1+I2-I3-I4 \\ -I1-I2+I3-I4 \\ -I1-I2-I3+I4 \end{bmatrix} \end{array}$$

$$\Downarrow$$

$$\begin{bmatrix} +I1-I2-I3-I4+V_N \\ -I1+I2-I3-I4+V_N \\ -I1-I2+I3-I4+V_N \\ -I1-I2-I3+I4+V_N \end{bmatrix} = \begin{bmatrix} DOUT1 \\ DOUT2 \\ DOUT3 \\ DOUT4 \end{bmatrix}$$

FIG. 11A $$\phantom{\frac{1}{4}} \quad \text{ENC1 ENC2 ENC3 ENC4}$$

$$\frac{1}{4} \begin{bmatrix} +1 & -1 & -1 & -1 \\ -1 & +1 & -1 & -1 \\ -1 & -1 & +1 & -1 \\ -1 & -1 & -1 & +1 \end{bmatrix} \times \begin{bmatrix} DOUT1 \\ DOUT2 \\ DOUT3 \\ DOUT4 \end{bmatrix} = \begin{bmatrix} I1+0.5\,V_N \\ I2+0.5\,V_N \\ I3+0.5\,V_N \\ I4+0.5\,V_N \end{bmatrix} = \begin{bmatrix} DATA1 \\ DATA2 \\ DATA3 \\ DATA4 \end{bmatrix}$$

FIG. 11B $$\begin{array}{c} \text{ENC1 ENC2 ENC3} \cdots \text{ENC8} \\ \begin{array}{c} T1 \\ T2 \\ T3 \\ \vdots \\ T8 \end{array} \begin{bmatrix} +1 & -1 & -1 & \cdots & -1 \\ -1 & +1 & -1 & \cdots & -1 \\ -1 & -1 & +1 & \cdots & -1 \\ \vdots & \vdots & \vdots & \ddots & \vdots \\ -1 & -1 & -1 & \cdots & +1 \end{bmatrix} \times \begin{bmatrix} I1 \\ I2 \\ I3 \\ \vdots \\ I8 \end{bmatrix} = \begin{bmatrix} AIN1 \\ AIN2 \\ AIN3 \\ \vdots \\ AIN8 \end{bmatrix} \end{array}$$

FIG. 12A $$\frac{1}{8} \begin{bmatrix} +1 & -1 & -1 & \cdots & -1 \\ -1 & +1 & -1 & \cdots & -1 \\ -1 & -1 & +1 & \cdots & -1 \\ \vdots & \vdots & \vdots & \ddots & \vdots \\ -1 & -1 & -1 & \cdots & +1 \end{bmatrix} \times \begin{bmatrix} DOUT1 \\ DOUT2 \\ DOUT3 \\ \vdots \\ DOUT8 \end{bmatrix} = \begin{bmatrix} I1+0.75V_N \\ I2+0.75V_N \\ I3+0.75V_N \\ \vdots \\ I8+0.75V_N \end{bmatrix} = \begin{bmatrix} DATA1 \\ DATA2 \\ DATA3 \\ \vdots \\ DATA8 \end{bmatrix}$$

FIG. 12B

SENSOR DEVICE AND MOBILE DEVICE INCLUDING THE SAME

CROSS-REFERENCE TO RELATED APPLICATION

This application claims benefit of priority to Korean Patent Application No. 10-2021-0015316, filed on Feb. 3, 2021, in the Korean Intellectual Property Office, the disclosure of which is incorporated herein by reference in its entirety.

BACKGROUND

1. Field

Embodiments relate to a sensor device and a mobile device including the same.

2. Description of the Related Art

Recently, a sensor device such as a biosensor, capable of collecting biometric information to provide useful services to users, tends to be mounted in wearable devices as well as mobile devices. A sensor device for collecting biometric information may include photodiodes generating electrical charges in response to light, and may perform signal processing on electrical charges, generated by the photodiodes, to determine biometric information.

SUMMARY

Embodiments are directed to a sensor device, including: a sensor array including a plurality of photodiodes configured to generate current signals in response to light; an encoder configured to encode the current signals to generate a plurality of analog signals and output the plurality of analog signals sequentially; a signal processing module configured to process the analog signals, received from the encoder, to generate digital signals; and a decoder configured to decode the digital signals, received from the signal processing module, to generate a plurality of data signals corresponding to the current signals.

Embodiments are also directed to a sensor device, including: a plurality of photodiodes configured to generate current signals in response to light; an encoder connected to the photodiodes through a plurality of analog channels, including a multiplier and an adder operating based on a predetermined orthogonal code, and configured to sequentially output a plurality of analog signals, obtained by encoding the current signals, to a single input channel; a signal processing module including an input terminal connected to the input channel and configured to successively output a plurality of digital signals corresponding to the analog signals, to an output terminal; a decoder connected to the output terminal and configured to output a plurality of data signals, obtained by decoding the digital signals according to an inverse matrix of an orthogonal matrix corresponding to the orthogonal code, to a plurality of digital channels; and a processor configured to generate information corresponding to the current signals using the data signals.

Embodiments are also directed to a mobile device including: a substrate; a plurality of photodiodes mounted on the substrate and configured to generate current signals in response to light incident from an object; a signal processing device mounted on the substrate and configured to convert the current signals into a plurality of data signals; and a processor configured to obtain biometric information using the data signals. The signal processing device is configured to convert a plurality of analog signals, generated using the current signals received through a plurality of input channels, into a plurality of digital signals sequentially, and generate the data signals using the digital signals.

BRIEF DESCRIPTION OF DRAWINGS

Features will become apparent to those of skill in the art by describing in detail example embodiments with reference to the attached drawings in which:

FIGS. 11A and 11B are diagrams illustrating an operation of a sensor device according to an example embodiment.

FIGS. 12A and 12B are diagrams illustrating an operation of a sensor device according to an example embodiment.

DETAILED DESCRIPTION

Figure 1:
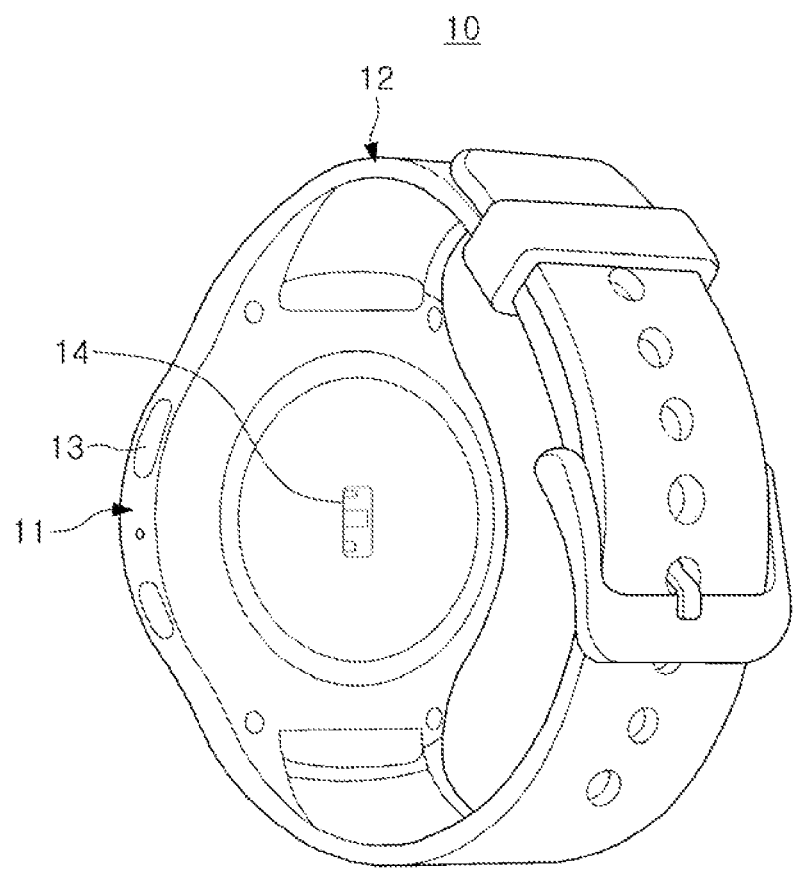
FIGS. 1 and 2 are schematic diagrams of mobile devices according to example embodiments, respectively.
Figure 2:
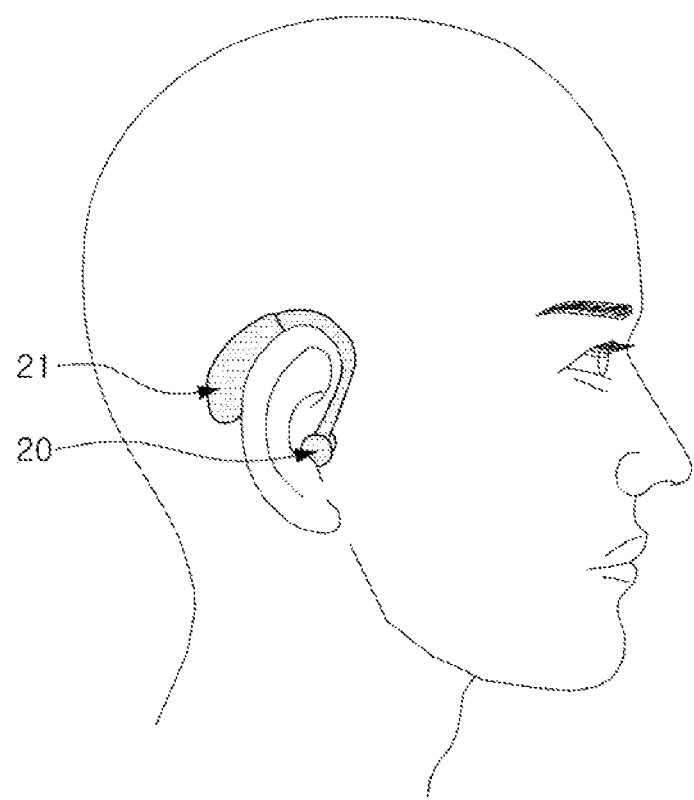

FIGS. 1 and 2 are schematic diagrams of mobile devices according to example embodiments, respectively.

Referring to FIG. 1, a mobile device 10 may be implemented as a watch-type wearable device. The mobile device 10 may include a housing or main body 11 and a strap 12 to fix the mobile device 10 to a user's body such as a wrist, and the like. A display, outputting a display image, may be provided on a front surface of the main body 11. Various application images, including time information, received message information, and the like, may be displayed on the display. According to an example embodiment, at least one of the front and side surfaces of the main body 11 may be provided with an input device 13 for receiving and processing a user input. The input device 13 may include a mechanical button or key, a touch panel, or the like.

A sensor device 14 may be disposed on a rear surface of the main body 11 facing the user's body. The sensor device 14 may include a light source emitting light to a user's body (such as a user wrist, to which the main body 11 may be fixed by the strap 12), at least one photodiode generating a current signal in response to light reflected from the user (e.g., the user's wrist), a signal processing module for processing the current signal, and the like. As an example, the mobile device 10 may determine biometric information, such as user heart rate, blood oxygen saturation, blood pressure, and the like, using a data signal output by the sensor device 14.

Referring to FIG. 2, a mobile device 20 may also be implemented as an ear-wearable device. The mobile device 20 may include an ear strap 21 or other fixed portion fixed to a user's body, and the user may hang the ear strap 21 on an auricle to wear the mobile device 20. In the state in which the user wears the mobile device 20, a main body of the mobile device 20 may be inserted into a user's external auditory meatus.

A sensor device may be mounted on the main body or the ear strap 21 of the mobile device 20. As an example, the sensor device may be provided on the ear strap 21 in contact with a user's skin to output light to the user's body and to detect light reflected from the user's body to output a digital signal. The mobile device 20 may determine user's biometric information using the digital signal, and may provide various applications using the biometric information.

Figure 3:
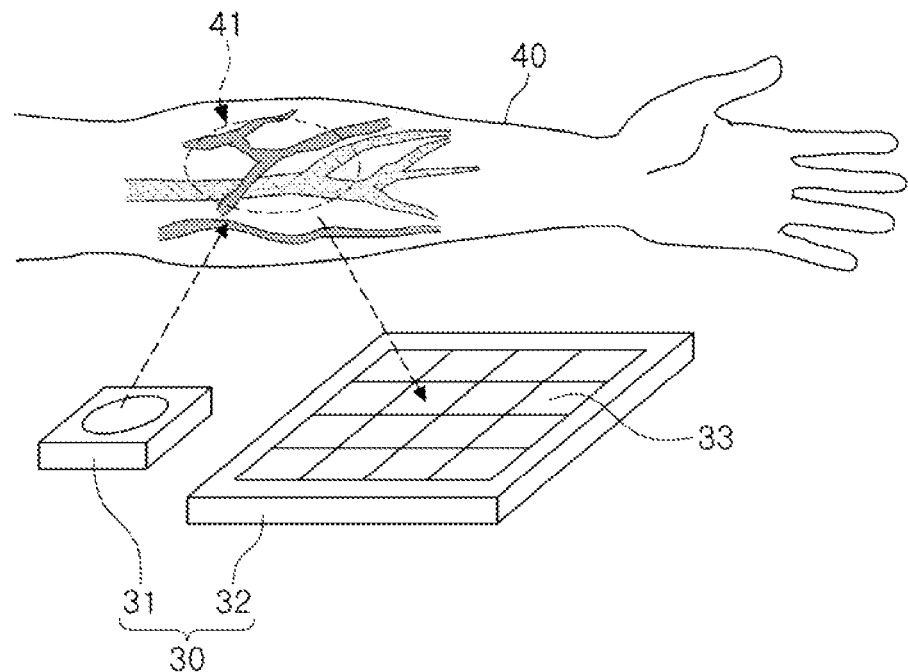
FIG. 3 is a schematic diagram of a sensor device according to an example embodiment.

FIG. 3 is a schematic diagram of a sensor device according to an example embodiment.

Referring to FIG. 3, a sensor device 30 according to an example embodiment may operate in a form proximate to a user's body 40, and may include a light emitting unit 31 and a sensor array 32. The sensor array 32 may include a plurality of sensing elements 33. As an example, each of the plurality of sensing elements may include a photodiode. As an example, the sensor device 30 may be a multi-channel optical sensor including a plurality of photodiodes, and may be a photoplethysmography (PPG) sensor or a spectrometer.

Referring to FIG. 3, the light emitting unit 31 may emit light toward the user's body 40. The light emitting unit 31 may include at least one light source. According to an example embodiment, the light source may emit light of a specific wavelength band. For example, a wavelength band of light emitted by the light source may vary depending on biometric information to be determined using the sensor device 30.

For example, when a heart rate is intended to be determined from the user's body 40, a light source outputting light of a green wavelength band may be included in the light emitting unit 31. In another example, when blood oxygen saturation is intended to be determined from the user's body 40, light sources outputting portions of light of a red wavelength band and an infrared wavelength band may be included in the light emitting unit 31. A plurality of light sources, emitting portions of light of different wavelength bands, may constitute the light emitting unit 31. The light emitting unit 31 may operate at least one of the plurality of light sources based on biometric information to be determined, and may obtain a signal from the sensor array 32.

In an example embodiment, the sensor array 32 may include a plurality of sensing elements 33 arranged in a matrix form. However, the arrangement form of the sensing elements 33 may vary according to an example embodiment. Each of the sensing elements 33 may include a photodiode which may generate a current signal in response to light. A signal processing module, included in the sensor device 30, may process a current signal to generate a digital signal. A processor of a mobile device, in which the sensor device 30 is mounted, may determine biometric information using the digital signal.

Figure 4:
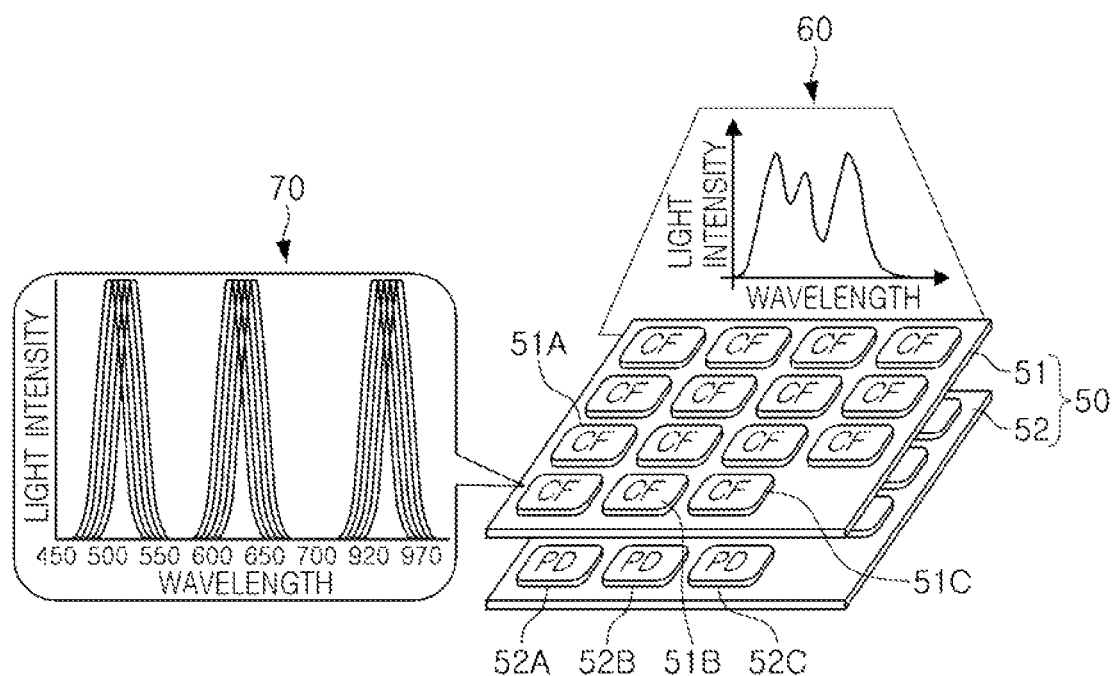
FIG. 4 is a diagram illustrating an operation of a sensor device according to an example embodiment.

FIG. 4 is a diagram illustrating an operation of a sensor device according to an example embodiment.

Referring to FIG. 4, a sensor array 50 of a sensor device according to an example embodiment may include a filter layer 51 and a photodiode layer 52. The filter layer 51 may include a plurality of color filters, and the photodiode layer 52 may include a plurality of photodiodes.

Light, emitted by a light emitting unit and reflected from a user's body, e.g., a blood vessel 41 in the user's body (see FIG. 3), may appear in all wavelength bands as illustrated in a first graph 60 of FIG. 4. However, as described above, light of a specific wavelength band may be selectively used depending on type of biometric information to be determined using a sensor device. To this end, the sensor array 50 may include a filter layer 51. The filter layer 51 may allow light of a specific wavelength band to selectively pass therethrough and may transmit the light to the photodiode layer 52, as illustrated in a second graph 70. Thus, the sensor device including the sensor array 50 according to an example embodiment illustrated in FIG. 4 may operate as a multi-wavelength PPG sensor.

Accordingly, sensitivity of the sensor device may be improved, light sources emitting portions of light of all wavelength bands may constitute a light emitting unit, and light of a required wavelength band may be selectively incident on a photodiode through the filter layer 51 to implement a sensor device which may determine various types of biometric information with a single light source. To this end, at least some of a plurality of color filters may allow portions of light of different wavelength bands to pass therethrough.

As an example, among the plurality of color filters, a first color filter 51A may allow only light of a green wavelength band to pass therethrough. The first color filter 51A may have a structure in which an infrared cutoff filter and a green color filter, allowing only light of a green wavelength band to pass therethrough, are stacked. Accordingly, among portions of light emitted from the light sources of the light emitting unit and reflected from a blood vessel, only the light of the green wavelength band may be incident on the first photodiode 52A below the first color filter 51A. The processor of the mobile device, in which the sensor device is mounted, may determine user's heart rate and pulse rate using a current signal output from the first photodiode 52A.

Among the plurality of color filters, a second color filter 51B may allow only light of a red wavelength band to pass therethrough, and a third color filter 51C may allow only light of an infrared wavelength band to pass therethrough. Therefore, among the portions of light emitted from the light source of the light emitting unit and reflected from the blood vessel, the light of the red wavelength band may be incident on the second photodiode 52B below the second color filter 51B, and the light of the infrared wavelength band may be incident on the lower third photodiode 52C below the third color filter 51C. The processor of the mobile device, in which the sensor device is mounted, may determine user's blood oxygen saturation using current signals output from the second photodiode 52B and the third photodiode 52C.

In order for a single sensor device to determine various types of biometric information, the sensor array 50 may include a filter layer 51 and a photodiode layer 52, as described with reference to FIG. 4. Photodiodes included in the photodiode layer 52 may be connected to a signal processing module, for processing a current signal, through a plurality of channels such that a current signal output by the sensor array 50 according to an example embodiment may be processed to determine desired biometric information. The signal processing module may be configured to independently process a current signal, received through a plurality of channels, to generate a digital signal. However, in this case, an area occupied by the signal processing module and power consumption of the signal processing module may be increased.

In an example embodiment, a sensor device may process current signals, generated by the sensor array 50, with one signal processing module. A sensor device according to an example embodiment may include an encoder, connected between an input terminal of a signal processing module and the sensor array 50, and a decoder connected to an output terminal of the signal processing module. The encoder may encode current signals, received through a plurality of channels, to generate analog signals, and may sequentially input the analog signals to the signal processing module. When the signal processing module sequentially processes analog signals to output digital signals, the decoder may generate data signals corresponding to the plurality of channels using the digital signals. Accordingly, the current signals received through the plurality of channels may be processed with a single signal processing module, and an area and power consumption of the sensor device may be reduced. In addition, an influence of noise generated in a process, in which the signal processing module converts a current signal into a data signal, may be reduced. This and other aspects of example embodiments are described in further detail below.

Figure 5:
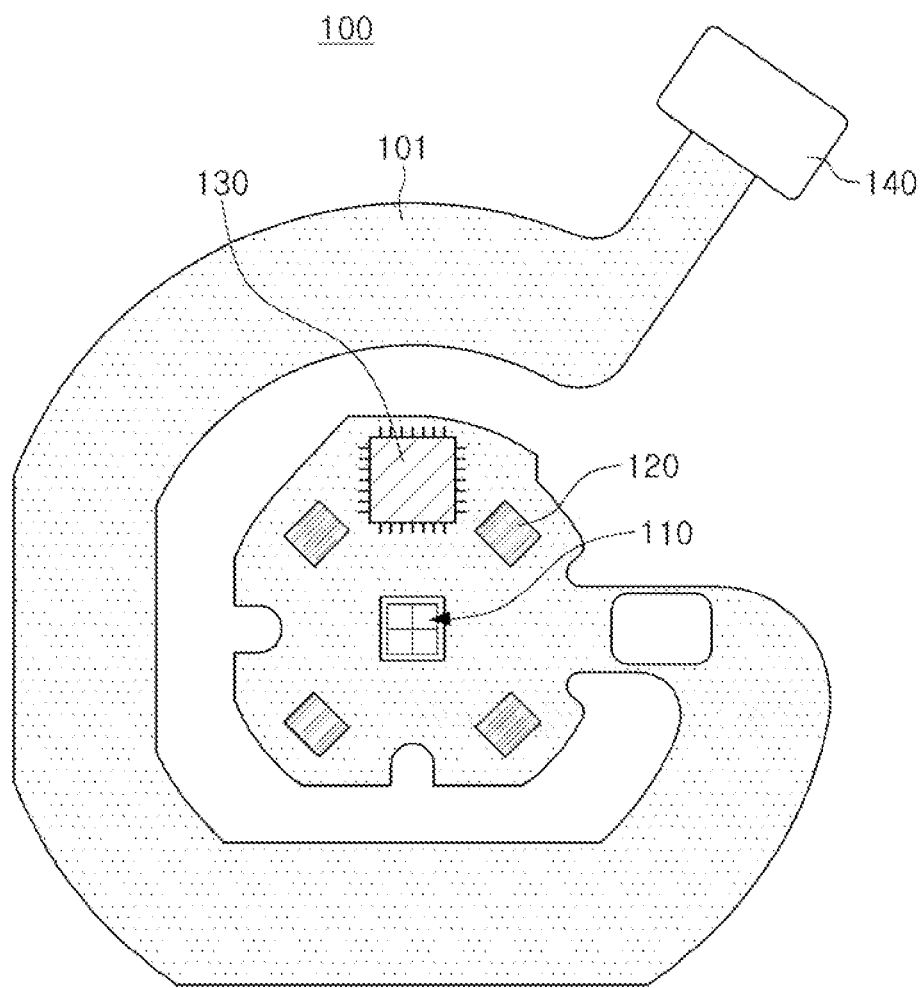
FIG. 5 is a schematic diagram of a sensor device according to an example embodiment.

FIG. 5 is a schematic diagram of a sensor device according to an example embodiment.

Referring to FIG. 5, a sensor device 100 according to an example embodiment may include a substrate 101, a light source 110 mounted on a first surface of the substrate 101, a plurality of photodiodes 120 mounted on the first surface together with the light source 110, a signal processing device 130, and the like. According to an example embodiment, the signal processing device 130 may be mounted on a second surface, facing away from the first surface, of the substrate 101. The substrate 101 may include a connector 140. A processor of a mobile device, in which the sensor device 100 is mounted, and the sensor device 100 may be electrically connected to each other through the connector 140.

Referring to FIG. 5, the photodiodes 120 may be disposed to be distributed around the light source 110. However, this is only an example embodiment, and the number and location of the photodiodes 120 may vary. As described above, a color filter allowing light of a specific wavelength band to selectively pass therethrough may be further disposed above the photodiodes 120.

Referring to FIG. 5, the sensor device 100 may include four photodiodes 120, and the signal processing device 130 may receive current signals from the photodiodes 120 through four channels.

According to the present example embodiment, the signal processing device 130 may include an encoder receiving the current signals through the four channels, a signal processing module processing analog signals output by the encoder to output digital signals, a decoder restoring data signals corresponding to four channels using the digital signals output by the signal processing module, and the like.

Figure 6:
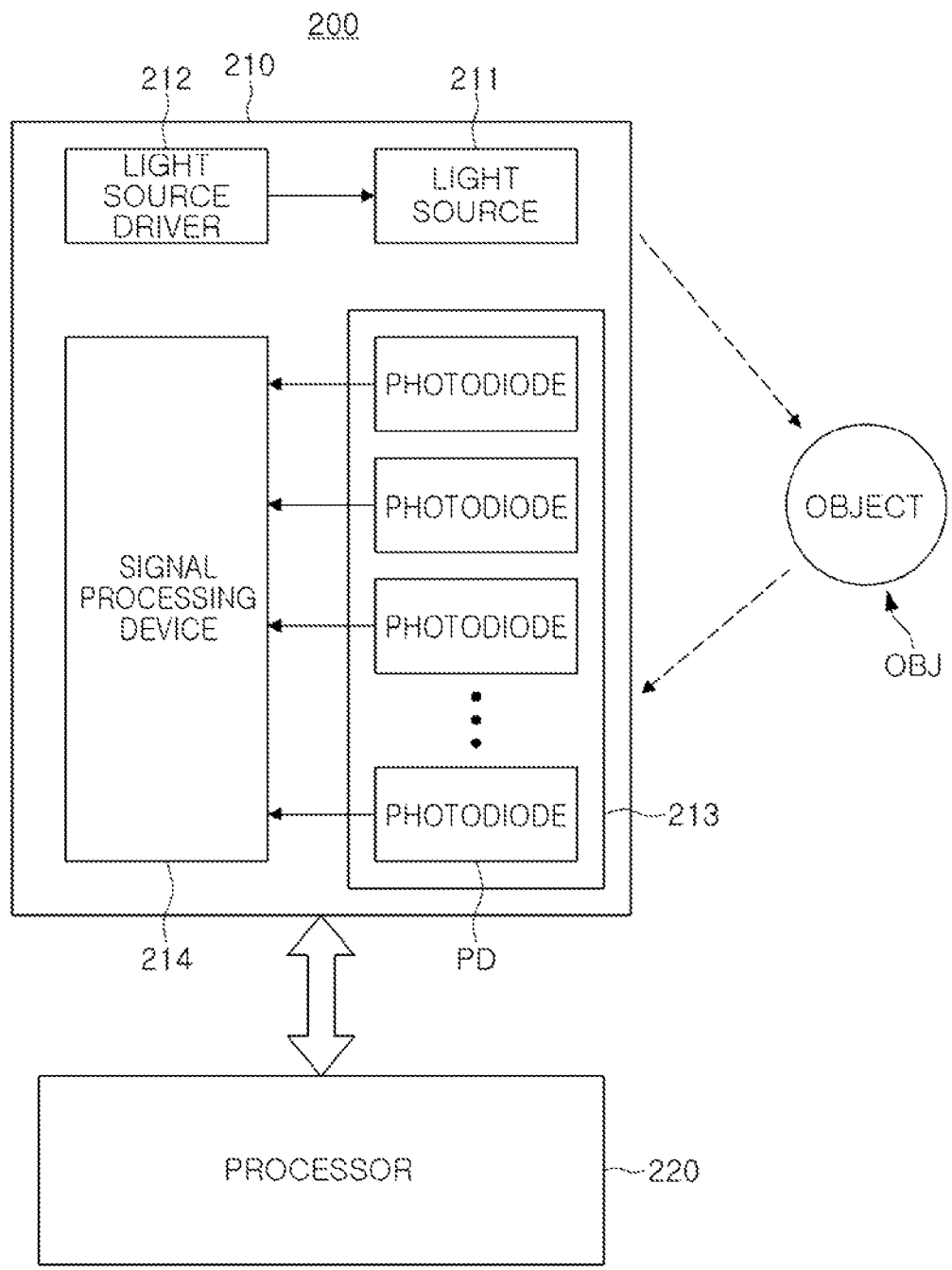
FIG. 6 is a schematic block diagram of a mobile device according to an example embodiment.

FIG. 6 is a schematic block diagram of a mobile device according to an example embodiment.

Referring to FIG. 6, a mobile device 200 according to an example embodiment may include a sensor device 210 and a processor 220. The processor 220 may be a semiconductor device controlling all operations of the mobile device 200, and may determine information related to an object OBJ using a digital signal output by the sensor device 210. As an example, when an object OBJ is a human body, the processor may determine information such as heart rate, blood oxygen saturation, blood pressure, and the like, and may execute various applications based on the information.

The sensor device 210 may include a light source 211, a light source driver 212, a sensor array 213, a signal processing device 214, and the like.

The light source 211 may emit light toward the object OBJ in response to a light control signal output from the light source driver 212. As an example, the light control signal output to the light source 211 by the light source driver 212 may be a pulse width modulation (PWM) signal. Accordingly, the light source 211 may be repeatedly turned on and off while the sensor device 210 is enabled to operate.

The sensor array 213 may include a plurality of photodiodes PD. According to an example embodiment, the sensor array 213 may further include a color filter allowing light of a predetermined wavelength band to be selectively incident on the photodiodes PD. The photodiodes PD may generate current signals in response to light emitted by the light source 211 and reflected from the object OBJ. According to an example embodiment, the light source 211 may be omitted. In this case, the photodiodes PD may generate current signals in response to light incident from the object OBJ, or the like.

The signal processing device 214 may convert current signals into digital signals and may output the digital signal to the processor 220. Since the light source 211 may be repeatedly turned on and off at a predetermined frequency while the sensor device 210 is enabled to operate, the signal processing device 214 may be synchronized with the light source driver 212 to obtain current signals from the photodiodes PD for a time for which the light source 211 is turned on. The signal processing device 214 may include an encoder receiving the current signals from the photodiodes PD of the sensor array 213 through respective channels, a signal processing module processing analog signals output by the encoder to output digital signals, a decoder restoring data signals corresponding to respective channels using the digital signals output by the signal processing module, and the like.

Figure 7:
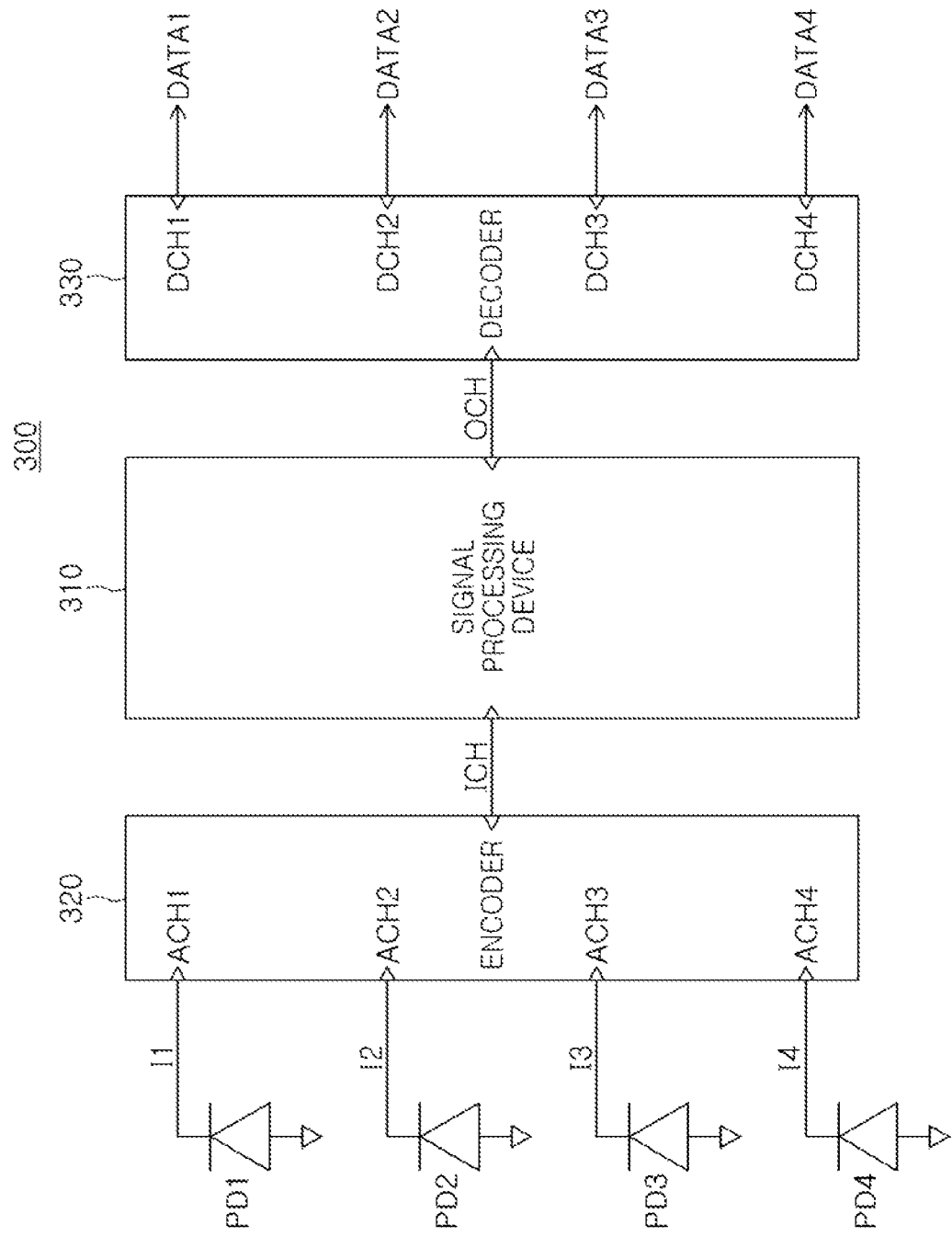
FIG. 7 is a schematic block diagram of a sensor device according to an example embodiment.

FIG. 7 is a schematic block diagram of a sensor device according to an example embodiment.

Referring to FIG. 7, a sensor device 300 according to an example embodiment may include a plurality of photodiodes PD1 to PD4, a signal processing module 310, an encoder 320, a decoder 330, and the like.

The photodiodes PD1 to PD4 may generate current signals I1 to I4 in response to external incident light. As an example, the photodiodes PD1 to PD4 may have incident thereon light that is emitted from an additional light source to generate the current signals I1 to I4 in response to light reflected from an object, and the object may be a part of a user's body. The current signals I1 to I4 may be input to the encoder 320 through a plurality of analog channels ACH1 to ACH4.

The encoder 320 may be connected to the photodiodes PD1 to PD4 through the analog channels ACH1 to ACH4, and may be connected to an input terminal of the signal processing module 310 through a single input channel ICH. The encoder 320 may encode current signals I1 to I4 to generate analog signals, and may sequentially input the analog signals to the signal processing module 310 through an input channel ICH. Accordingly, the signal processing module 310 may sequentially receive the analog signals through the input channel ICH. Each of the analog signals, encoded by the encoder 320, may be a signal including the current signals I1 to I4 and may be a signal obtained by encoding the current signals I1 to I4 based on a predetermined orthogonal code.

The signal processing module 310 may process the sequentially input analog signals to generate digital signals. As an example, the encoder 320 may generate four analog signals using the four current signals I1 to I4, and the signal processing module 310 may convert the four analog signals into a digital domain to output four digital signals. The signal processing module 310 may sequentially output the four digital signals to the decoder 330 through a single output channel OCH connected to the output terminal.

The decoder 330 may generate data signals DATA1 to DATA4 using digital signals. The data signals DATA1 to DATA4 may be output through the plurality of digital channels DCH1 to DCH4, respectively. Each of the data signals DATA1 to DATA4 may be obtained by converting each of the current signals I1 to I4 into a digital domain. For example, the first data signal DATA1 may be obtained by converting the first current signal I1 into a digital domain, and the second data signal DATA2 may obtained by converting the second current signal I2 into a digital domain.

The decoder 330 may generate the data signals DATA1 to DATA4 based on an orthogonal code used when the encoder 320 encodes the current signals I1 to I4 to generate the analog signals. As an example, the decoder 330 may restore the data signals DATA1 to DATA4 from digital signals using an inverse matrix of an orthogonal matrix corresponding to the orthogonal code.

The signal processing module 310 may be an analog-front end (AFE) module. The signal processing module 310 may include a current-to-voltage converter converting analog signals generated from the current signals I1 to I4 into a voltage, an amplifier amplifying analog signals, an analog-to-digital converter (ADC), and the like. Hereinafter, the signal processing module 310 will be described in more detail with reference to FIG. 8.

Figure 8:
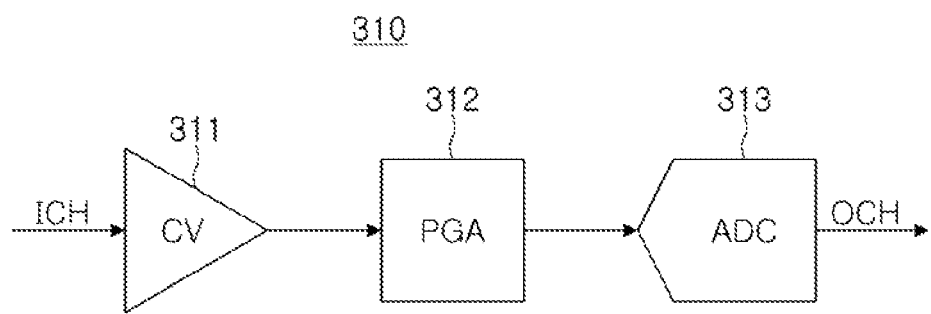
FIG. 8 is a schematic diagram of a signal processing module included in a sensor device according to an example embodiment.

FIG. 8 is a schematic diagram of a signal processing module included in a sensor device according to an example embodiment.

Referring to FIG. 8, the signal processing module 310 according to an example embodiment may include a current-to-voltage converter 311, an amplifier 312, an analog-to-digital converter 313, and the like. The current-to-voltage converter 311 may be a circuit converting analog signals, sequentially received through the input channel ICH, into a voltage and may include, e.g., an operational amplifier, a feedback resistor, and the like. A voltage signal output by the current-to-voltage converter 311 may be transmitted to the amplifier 312, and the amplifier 312 may include a programmable gain amplifier.

The analog-to-digital converter 313 may convert the voltage signal, output by the amplifier 312, into a digital domain to generate a digital signal, and may output the digital signal through the output channel OCH. In an operation of the signal processing module 310, analog signals may be sequentially input by an encoder connected to an input terminal of the signal processing module 310, and the analog-to-digital converter 313 may sequentially output digital signals corresponding to the analog signals.

Figure 9:
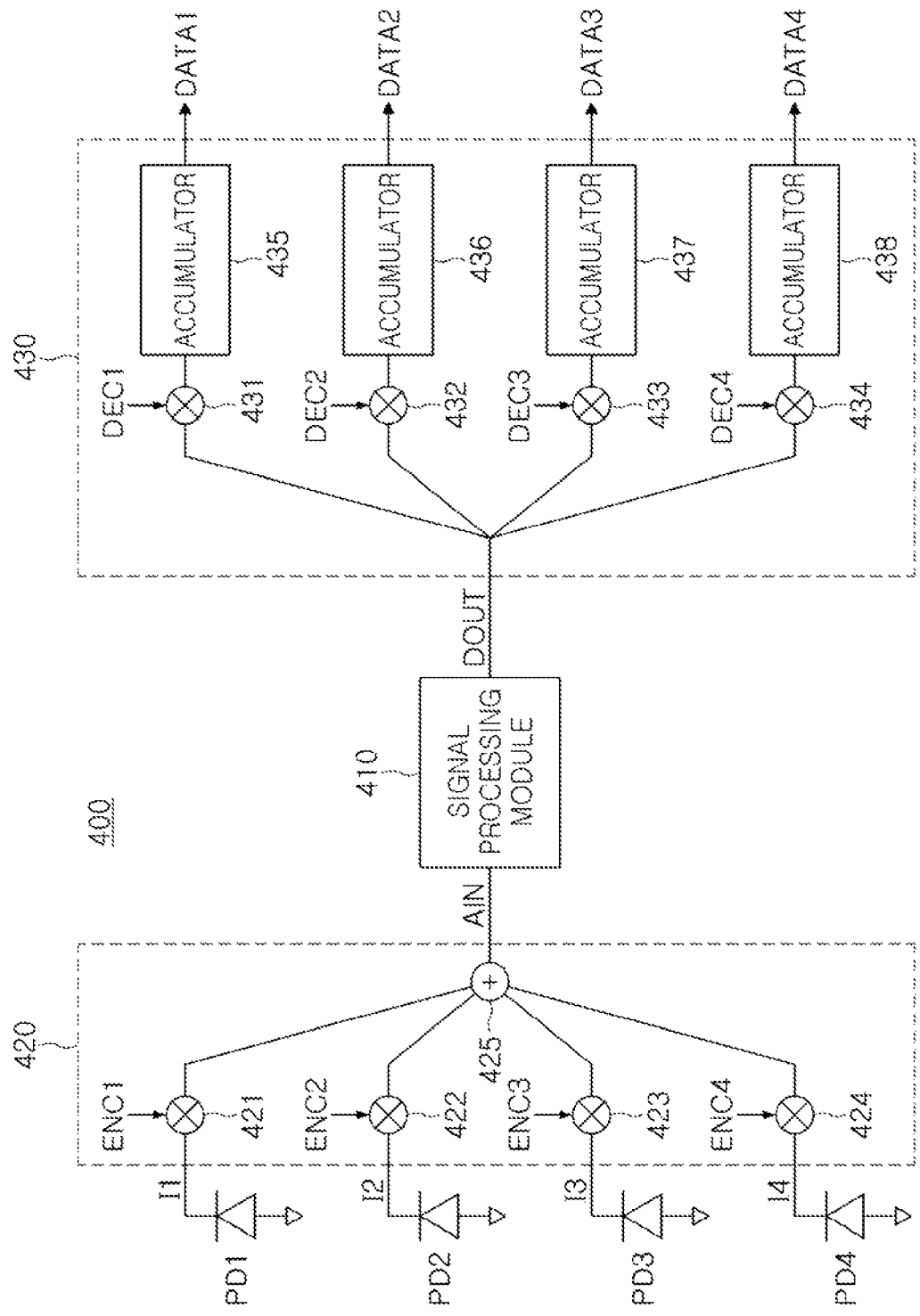
FIG. 9 is a schematic diagram of a sensor device according to an example embodiment.

FIG. 9 is a schematic diagram of a sensor device according to an example embodiment.

Referring to FIG. 9, a sensor device 400 according to an example embodiment may include a signal processing module 410, an encoder 420, a decoder 430, and the like. The encoder 420 may be connected to a plurality of photodiodes PD1 to PD4, and may encode current signals I1 to I4 to generate analog signals AIN. The analog signals AIN may be sequentially input to the signal processing module 410.

The signal processing module 410 may digitally convert analog signals AIN to generate digital signals DOUT. The digital signals DOUT may be input to the decoder 430, and the decoder 430 may generate data signals DATA1 to DATA4 using the digital signals DOUT. As an example, the data signals DATA1 to DATA4 may correspond to current signals I1 to I4 generated by the photodiodes PD1 to PD4, respectively.

In the example embodiment illustrated in FIG. 9, the encoder 420 may include a plurality of multipliers 421 to 424 and an adder 425. The multipliers 421 to 424 may respectively receive encoding coefficients ENC1 to ENC4, and may output signals obtained by multiplying the current signals I1 to I4 by the encoding coefficients ENC1 to ENC4. The encoding coefficients ENC1 to ENC4 may not be zero. The adder 425 may sum the multiplied signals (i.e., the signals resulting from the multiplication of the encoding coefficients ENC1 to ENC4 with the current signals I1 to I4) to generate the analog signals AIN.

The encoding coefficients ENC1 to ENC4 may be determined by an orthogonal code used when the encoder 420 encodes the current signals I1 to I4 to generate the analog signals AIN. As an example, values of the encoding coefficients ENC1 to ENC4 may be changed while the plurality of photodiodes PD1 to PD4 output the current signals I1 to I4. When the number of the photodiodes PD1 to PD4 is four, the encoder 420 may divide output time of the current signals I1 to I4 into four unit times (the unit times may have a duration corresponding to a time in which the signal processing module converts each of the analog signals into a digital domain), and at least one of the encoding coefficients ENC1 to ENC4 may be set to different values in the unit times (the encoding coefficients ENC1 to ENC4 and an operation of the encoder 420 depending thereon will be described below with reference to FIG. 10).

Still referring to FIG. 9, the decoder 430 may include a plurality of multipliers 431 to 434 and a plurality of accumulators 435 to 438. For example, one of the multipliers 431 to 434 and one of the accumulators 435 to 438 may be assigned to each of the digital channels outputting the data signals DATA1 to DATA4.

The multipliers 431 to 434 may respectively receive decoding coefficients DEC1 to DEC4, and may multiply each of the sequentially output digital signals DOUT by the decoding coefficients DEC1 to DEC4. The accumulators 435 to 438 may sequentially accumulate and sum the digital signals DOUT, obtained by multiplying the decoding coefficients DEC1 to DEC4, to generate data signals DATA1 to DATA4.

The decoding coefficients DEC1 to DEC4 may be determined by an inverse matrix of an orthogonal code used by the encoder 420. In an example embodiment, an absolute value of each of the decoding coefficients DEC1 to DEC4 may be smaller than an absolute value of each of the encoding coefficients ENC1 to ENC4.

Hereinafter, an example operation of the sensor device 400 will be described in detail with reference to FIGS. 10, 11A, and 11B.

Figure 10:
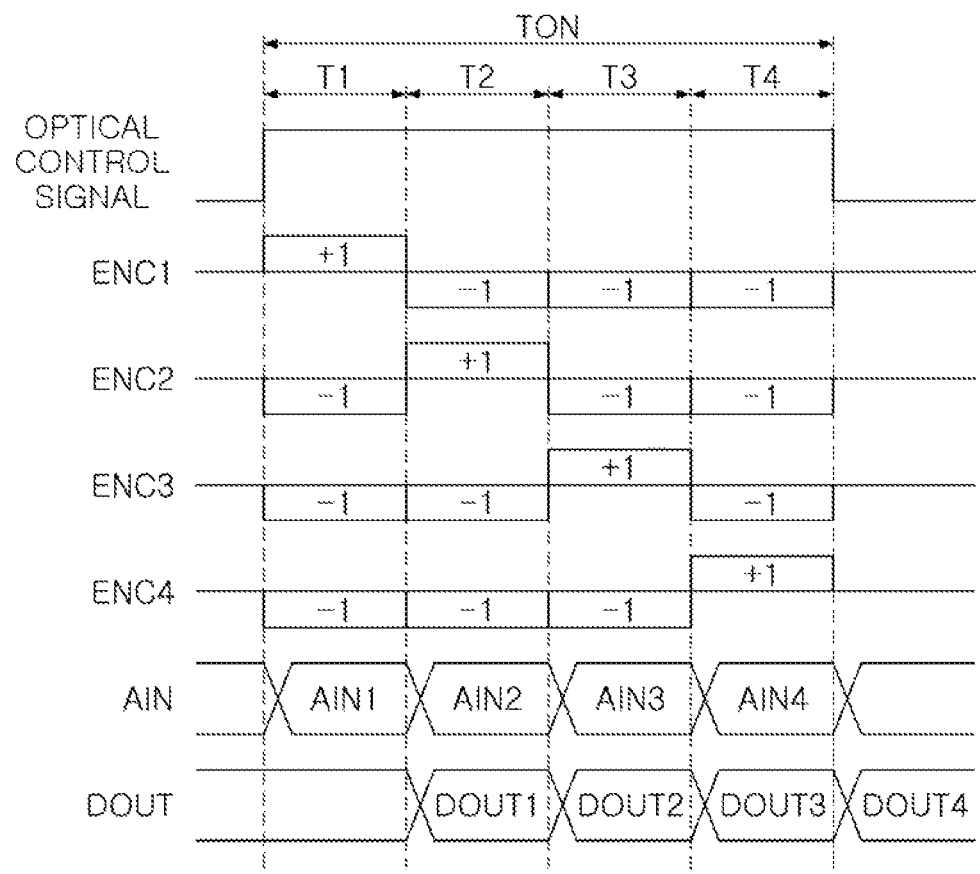
FIG. 10 is a timing diagram illustrating an operation of a sensor device according to an example embodiment.

FIG. 10 is a timing diagram illustrating an operation of a sensor device according to an example embodiment, and FIGS. 11A and 11B are diagrams illustrating an operation of a sensor device according to an example embodiment.

Referring to FIG. 10, the photodiodes PD1 to PD4 may output current signals I1 to I4 during a light emitting time TON during which a light source is turned on by a light control signal. The sensor device 400 may divide the light emitting time TON into a plurality of unit times T1 to T4, and the encoder 420 may adjust the encoding coefficients ENC1 to ENC4 at each of the unit times T1 to T4 to generate analog signals AIN.

As an example, during the first unit time T1, the encoding coefficients ENC1 to ENC4 may be determined as [+1, −1, −1, −1]. Thus, during the first unit time T1, a first analog signal AIN1 input to the signal processing module 410 may be determined as [I1−I2−I3−I4]. During the next second unit time T2, the encoding coefficients ENC1 to ENC4 may be determined as [−1, +1, −1, −1], and thus the signal processing module 410 may receive a second analog signal AIN2 defined as [−I1+I2−I3−I4]. Similarly, during the third unit time T3, a third analog signal AIN3 input to the signal processing module 410 may be represented by [−I1−I2+I3−I4], and a fourth analog signal AIN4 input to the signal processing module 410 may be represented by [−I1−I2−I3+I4].

The signal processing module 410 may sequentially convert the first to fourth analog signals AIN1 to AIN4 to digital domains to output first to fourth digital signals DOUT1 to DOUT4. Output timings of the first to fourth digital signals DOUT1 to DOUT4 may be determined as illustrated in FIG. 10 by time required for the signal processing module 410 to convert each of the first to fourth analog signals AIN1 to AIN4 into a digital domain. A delay time (i.e., a difference between an input time of the first to fourth analog signals AIN1 to AIN4 and an output time of the first to fourth digital signals DOUT1 to DOUT4) may vary depending on the configuration of the signal processing module 410.

The encoding code, used when the encoder 420 encode the current signals I1 to I4 to generate the analog signals AIN, may be a code generated based on an orthogonal code and may be represented by an orthogonal matrix, e.g., an N-by-N matrix where N is a number of photodiodes (where N is a positive integer of 2 or more). As an example, in the example embodiment described with reference to FIG. 10, the encoding code may be represented by Equation 1 below. Rows of the encoding code may respectively correspond to unit times T1 to T4, and columns may respectively correspond to encoding coefficients ENC1 to ENC4. As illustrated in Equation 1, the encoding coefficients ENC1 to ENC4 may not be zero.

$$\text{Encoding Code} = \begin{bmatrix} +1 & -1 & -1 & -1 \\ -1 & +1 & -1 & -1 \\ -1 & -1 & +1 & -1 \\ -1 & -1 & -1 & +1 \end{bmatrix} \quad \text{Equation 1}$$

Additionally, the decoding coefficients DEC1 to DEC4, used by the decoder 430 to restore the data signals DATA1 to DATA4 from the digital signals DOUT, may be determined by a decoding code represented by an inverse matrix of an orthogonal matrix. As an example, a decoding code corresponding to the encoding code expressed in Equation 1 may be represented by Equation 2 below. In the decoding code, columns may correspond to decoding coefficients DEC1 to DEC4, respectively. As illustrated in Equations 1 and 2, an absolute value of each of the decoding coefficients DEC1 to DEC4 may be smaller than an absolute value of each of the encoding coefficients ENC1 to ENC4.

$$\text{Decoding Code} = \frac{1}{4}\begin{bmatrix} +1 & -1 & -1 & -1 \\ -1 & +1 & -1 & -1 \\ -1 & -1 & +1 & -1 \\ -1 & -1 & -1 & +1 \end{bmatrix} \quad \text{Equation 2}$$

Hereinafter, operations of the encoder 420 and the decoder 430 will be described in more detail with reference to FIGS. 11A and 11B.

FIG. 11A is a diagram for describing an operation of the encoder 420.

Referring to FIG. 11A, current signals I1 to I4 generated by photodiodes PD1 to PD4 may be represented by a matrix, and first to fourth analog signals AIN1 to AIN4 may be generated as a result of an operation of an encoding code on the current signals I1 to I4.

For example, the first to fourth analog signals AIN1 to AIN4 may be sequentially input to the signal processing module 410, and the signal processing module 410 may digitally convert each of the first to fourth analog signals AIN1 to AIN4 to sequentially output first to fourth digital signals DOUT1 to DOUT4. Correspondingly, noise may be generated during the operation in which the signal processing module 410 digitally converts the first to fourth analog signals AIN1. Accordingly, each of the first to fourth digital signals DOUT1 to DOUT4 may include a predetermined noise component $V_N$ (in FIG. 11A, the first to fourth digital signals DOUT1 to DOUT4 are illustrated as including noise components $V_N$ having the same size, but at least some of the signals DOUT1 to DOUT4 may include noise components VN having different sizes).

FIG. 11B is a diagram for describing an operation of the decoder 430.

Referring to FIG. 11B, the operation of the decoder 430 may be represented by a decoding code. While the signal processing module 410 outputs the first digital signal DOUT1, digital coefficients DEC1 to DEC4 may be defined as [+¼, −¼, −¼, −¼]. Thus, +¼*DOUT1 may be input to the first accumulator 435, and −¼*DOUT1 may be input to each of the second to fourth accumulators 436 to 438. Next, while the signal processing module 410 outputs the second digital signal DOUT2, the digital coefficients DEC1 to DEC4 may be determined as [−¼, +¼, −¼, −¼], and thus +¼*DOUT2 may be input to the second accumulator 436, and −¼*DOUT2 may be input to each of the first, third, and fourth accumulators 435, 437, and 438. While the signal processing module 410 outputs the third digital signal DOUT3, the digital coefficients DEC1 to DEC4 may be determined as [−¼, −¼, +¼, −¼], and thus +¼*DOUT3 may be input to the third accumulator 437, and −¼*DOUT3 may be input to each of the first, second, and fourth accumulators 435, 436, and 438. Finally, while the signal processing module 410 outputs the fourth digital signal DOUT4, the digital coefficients DEC1 to DEC4 may be determined as [−¼, −¼, −¼, +¼], and thus +¼*DOUT4 may be input to the fourth accumulator 438, and −¼*DOUT4 may be input to each of the first to third accumulators 435 to 437.

As described above, after the signal processing module 410 outputs to the fourth digital signal DOUT4, signals that are accumulated and summed in each of the accumulators 435 to 438 may be represented by Equation 3 below.

1st Accumulator=¼*(DOUT1−DOUT2−DOUT3−DOUT4)

2nd Accumulator=¼*(−DOUT1+DOUT2−DOUT3−DOUT4)

3rd Accumulator=¼*(−DOUT1−DOUT2+DOUT3−DOUT4)

4th Accumulator=¼*(−DOUT1−DOUT2−DOUT3+DOUT4)     Equation 3

The digital signals DOUT1 to DOUT4, output from the signal processing module 410, may include the noise component $V_N$ and may be defined as described above with reference to FIG. 11A. When the digital signals DOUT1 to DOUT4 described with reference to FIG. 11A are applied to Equation 3, the data signals DATA1 to DATA4 output from the accumulators 435 to 438 may be defined as illustrated in FIG. 11B. I can. In other words, each of the data signals DATA1 to DATA4 may include data, obtained by converting each of the current signals I1 to I4 into a digital domain, and a noise component $0.5V_N$ that is averaged to be reduced by the operation of the decoder 430.

In an example embodiment, the encoder 420 and the decoder 430 may be respectively connected to an input terminal and an output terminal of the signal processing module 410, and the encoder 420 may input the current signals I1 to I4, received through a plurality of analog channels, to the signal processing module 410. The signal processing module 410 may convert analog signals AIN into digital signals DOUT, and then may sequentially output the digital signals DOUT to the decoder 430. In this case, a predetermined noise component $V_N$ may be reflected in each of the digital signals DOUT. The noise component $V_N$ may be canceled and/or reduced while the decoder 430 restores the data signals DATA1 to DATA4 corresponding to the current signals I1 to I4 using the digital signals DOUT. Accordingly, the sensor device 400 may be implemented having improved signal-to-noise ratio (SNR) characteristics.

The configurations of the encoding code and the decoding code for the operations of the encoder 420 and the decoder 430 are not limited to those described with reference to FIGS. 10, 11A, and 11B. The encoding coefficients ENC1 to ENC4 and the decoding coefficients DEC1 to DEC4, respectively defining the encoding code and the decoding code, may be freely selected under conditions satisfying the characteristics of an orthogonal code. A size of a matrix, representing the encoding code and the decoding code, may be determined depending on a number of sensing elements, e.g., a number of photodiodes PD connected to the signal processing module 410.

FIGS. 12A and 12B are diagrams illustrating an operation of a sensor device according to an example embodiment.

Referring to FIGS. 12A and 12B, a sensor device may include eight sensing components. Therefore, as illustrated in FIG. 12A, an encoding code may be represented by an 8-by-8 matrix. In the embodiment illustrated in FIG. 12A, all diagonal components of the encoding code may be +1, and all other components may be −1. However, this is only an example embodiment, and components of the encoding code may vary under conditions satisfying characteristics of the orthogonal code.

The sensor device may divide a light emitting time, during which a light source emits light, into eight unit times T1 to T8. At least some of encoding coefficients ENC1 to ENC8 may have different values in each of the unit times T1 to T8, and a signal processing module may sequentially receive eight analog signals AIN1 to AIN8 generated by the encoder during the emission time.

FIG. 12B is a diagram for describing an operation of a decoder.

Referring to FIG. 12B, a decoding code may be an inverse matrix of the encoding code, and may be represented by an 8-by-8 matrix. Digital signals DOUT1 to DOUT8, respectively obtained by digitally converting analog signals AIN1 to AIN8 by the signal processing module, may be restored to data signals DATA1 to DATA8 by the decoding code. As an example, each of the data signals DATA1 to DATA8 may include data, obtained by converting each of the current signals I1 to I8 into a digital domain, and a noise component $0.75V_N$ averaged to be reduced by the decoder.

Accordingly, noise characteristic of the sensor device may be improved, as compared with the case in which the encoder and the decoder are not applied. In addition, a single signal processing module may process current signals output from a plurality of sensing elements, so that the degree of integration of the sensor device may be increased and power consumption may be reduced.

Figure 13:
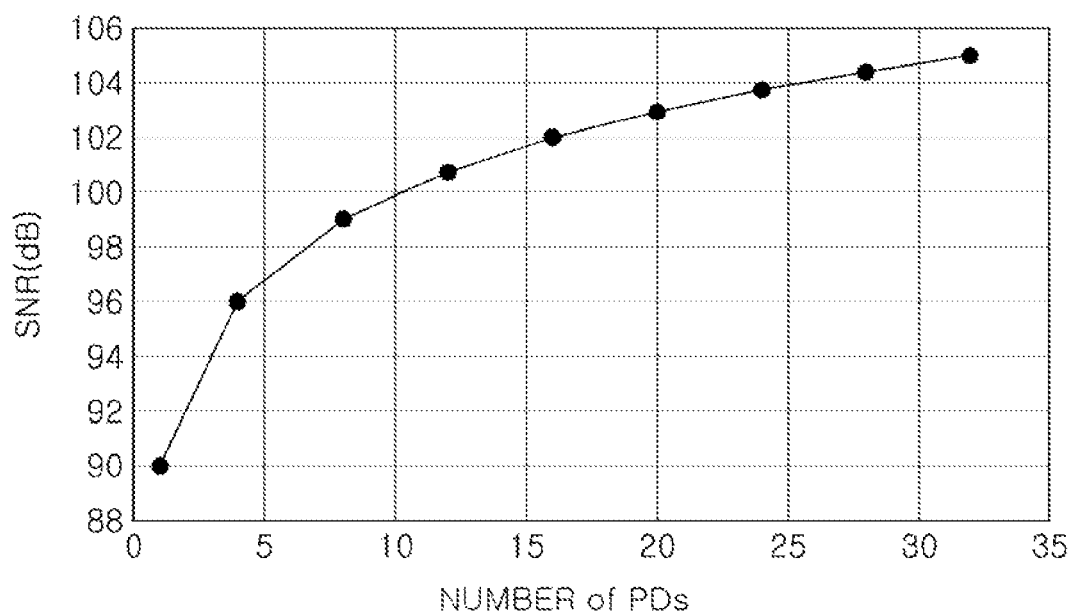
FIG. 13 is a graph illustrating an operation of a sensor device according to an example embodiment.

FIG. 13 is a graph illustrating an operation of a sensor device according to an example embodiment.

Referring to FIG. 13, as the number of photodiodes included in a sensor device increases, a signal-to-noise ratio (SNR) of the sensor device may increase. For example, an SNR when a current signal generated by four photodiodes is used (96 dB) may be improved by about 6 dB, as compared with an SNR when a signal processing module generates a data signal using a current signal generated by a single photodiode (90 dB). In addition, when a data signal is generated using a current signal generated by eight photodiodes, an SNR (99 dB) may be improved by about 9 dB relative to the single photodiode (90 dB). As a result, the SNR may be improved and performance of the sensor device may be improved by increasing the number of photodiodes emitting light and generating a current signal in response to light reflected from a user's body or the like.

However, as the number of photodiodes increases, the number of channels connecting the signal processing module and the photodiodes may also increase, and power consumption of the signal processing module and a circuit area occupied by the signal processing module may increase. In an example embodiment, this issue may be addressed by respectively connecting an encoder and a decoder to an input terminal and an output terminal of a signal processing module. Then, current signals, generated by photodiodes, may be sequentially input to a signal processing module after being encoded into analog signals by an encoder, and the signal processing module may sequentially output digital signals. The decoder may restore data signals using the sequentially output digital signals. Accordingly, only one signal processing module may process current signals of photodiodes connected to a plurality of channels, so that power consumption and circuit area of the sensor device may be reduced and manufacturing costs of the sensor device may be reduced.

In another example embodiment, the sensor device may include two or more signal processing modules. For example, when N photodiodes are connected through N channels, the N photodiode may be divided by half and then N/2 photodiodes may be distributed and connected to each of the two signal processing modules. In this case, the number of photodiodes connected to each of the signal processing modules and the number of current signals to be processed by each of the signal processing modules accordingly may be decreased to improve an operation speed of the sensor device.

Figure 14:
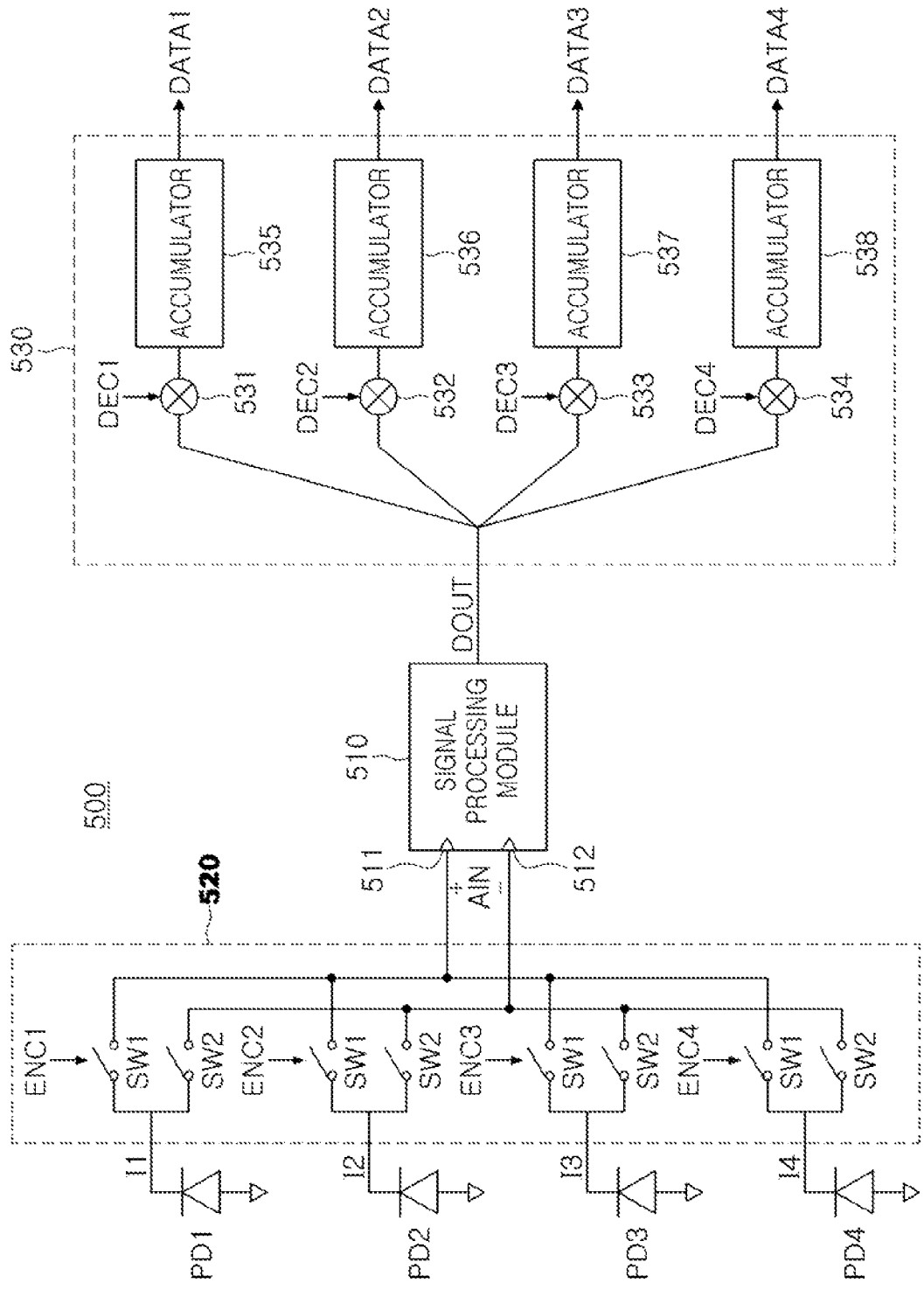
FIG. 14 is a schematic diagram of a sensor device according to an example embodiment.

FIG. 14 is a schematic diagram of a sensor device according to an example embodiment.

In the example embodiment illustrated in FIG. 14, a sensor device 500 may include a plurality of photodiodes PD1 to PD4, a signal processing module 510, an encoder 520, a decoder 530, and the like. As described above, the number of photodiodes PD1 to PD4 may vary.

The encoder 520 may include a plurality of pairs of switches SW1 and SW2, e.g., a positive switch and a negative switch, respectively. Each of the photodiodes PD1 to PD4 may be connected to one of the pairs of switches SW1 and SW2.

Activation, e.g., a turn-on/off, of the pair of switches SW1 and SW2 may be determined by encoding coefficients ENC1 to ENC4.

As an example, the pair of switches SW1 and SW2 may not both be turned on at the same time. For example, when the first switch SW1 of the pair of switches SW1 and SW2 is turned on, the second switch SW2 may be turned off. Meanwhile, when the second switch SW2 is turned on, the first switch SW1 may be turned off.

Referring to FIG. 14, the signal processing module 510 may receive analog signals in a differential signal manner through a positive input terminal 511 and a negative input terminal 512. The first switch SW1 may be connected to the positive input terminal 511, and the second switch SW2 may be connected to the negative input terminal 512.

The operation of the encoder 520 may be similar to that described with reference to FIGS. 10 and 11A. For example, the first switch SW1 connected to the first photodiode PD1 may be turned on by the first encoding coefficient ENC1 for a first unit time, and the second switch SW2 connected to the second to fourth photodiodes PD2 to PD4 by the second to fourth encoding coefficients ENC2 to ENC4 may be turned on. Accordingly, the analog signal AIN input to the signal processing module 510 for the first unit time may be defined as [I1−I2−I3−I4]. Similarly, for the second unit time, the second switch SW2 connected to the second photodiode PD2 may be turned on, and the first switch SW1 connected to the first, third, and fourth photodiodes PD1, PD3, and PD4 may be turned on. Accordingly, the encoder 520 may operate in a similar manner as described with reference to FIGS. 10 and 11A. The operation of the decoder 530 may also be similar to the operation described with reference to FIG. 11B.

Figure 15:
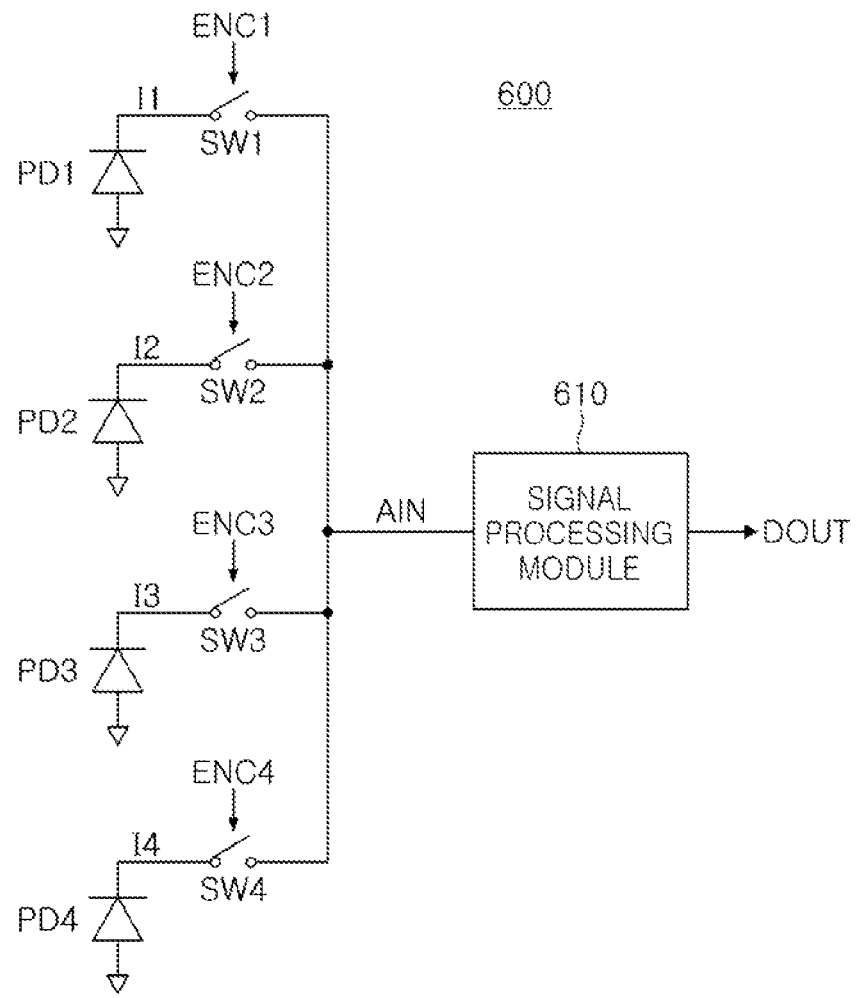
FIGS. 15 to 17 are diagrams illustrating a comparative example of a sensor device.
Figure 16:
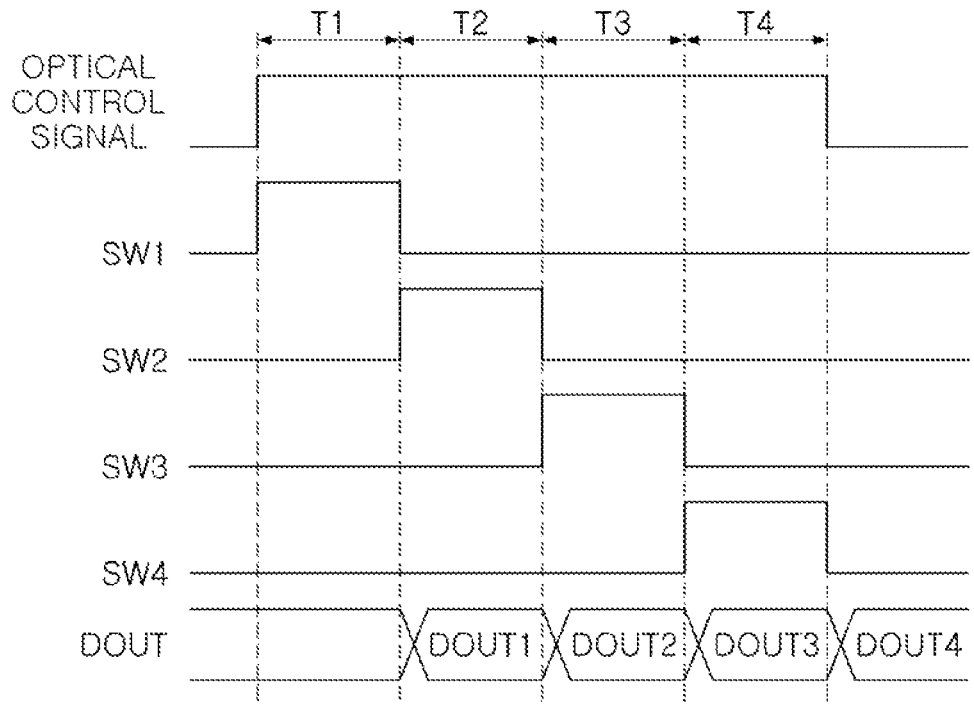
Figure 17:
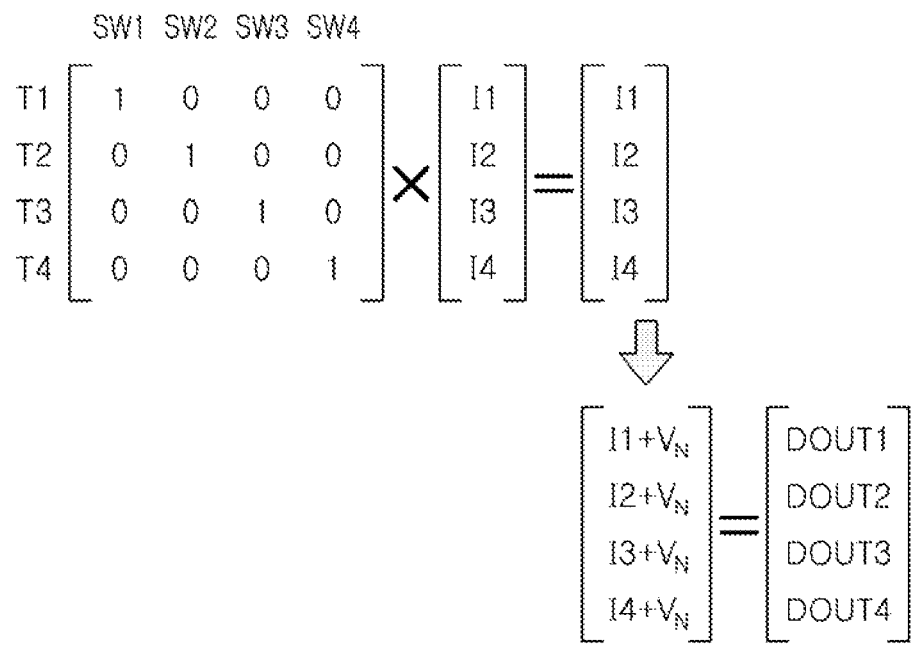

FIGS. 15 to 17 are diagrams illustrating a comparative example of a sensor device.

Referring to FIG. 15, in a sensor device 600 according to a comparative example, a signal processing module 610 may convert an analog signal AIN into a digital signal DOUT. A plurality of photodiodes PD1 to PD4 may be connected to an input terminal of the signal processing module 610 through a plurality of switches SW1 to SW4.

FIG. 16 is a timing diagram for describing an operation of the sensor device 600.

Referring to FIG. 16, first to fourth switches SW1 to SW4 may be sequentially turned on at first to fourth timings T1 to T4, respectively. Accordingly, the first to fourth current signals I1 to I4 may be sequentially input to the signal processing module 610, and the signal processing module 610 may sequentially output digital signals DOUT1 to DOUT4 corresponding to the first to fourth current signals I1 to I4.

The operation of the sensor device 600 may be represented as a matrix illustrated in FIG. 17.

Referring to FIG. 17, the operations of the first to fourth switches SW1 to SW4 during the first to fourth timings T1 to T4 may be represented by a matrix in which all diagonal components are 1 and the other components are 0. During the first timing T1, only the first switch SW1 may be turned on to input the first current signal I1 to the signal processing module 610, and the signal processing module 610 may digitally convert the first current signal I1 to generate a first digital signal DOUT1. Operations, similar to the above operations, may be performed in each of the second to fourth timings T2 to T4.

Accordingly, a noise component $V_N$ generated in the operation of the signal processing module 610 may be reflected in the first to fourth digital signals DOUT1 to DOUT4 as it is. In the comparative example (in which an encoder and a decoder are not connected to an input terminal and an output terminal of the signal processing module 610, unlike the above-described example embodiments), it is not expected that the noise component $V_N$ generated in the operation of the signal processing module 610 will be averaged to be reduced. Relative to the comparative example, referring to FIGS. 11A and 11B illustrating an example embodiment including four photodiodes PD1 to PD4, the noise component $V_N$ may be averaged by a decoder to be reduced by half as compared with the comparative example. Accordingly, a sensor device having an improved signal-to-noise ratio (SNR) and improved noise characteristics may be implemented according to example embodiments.

Figure 18:
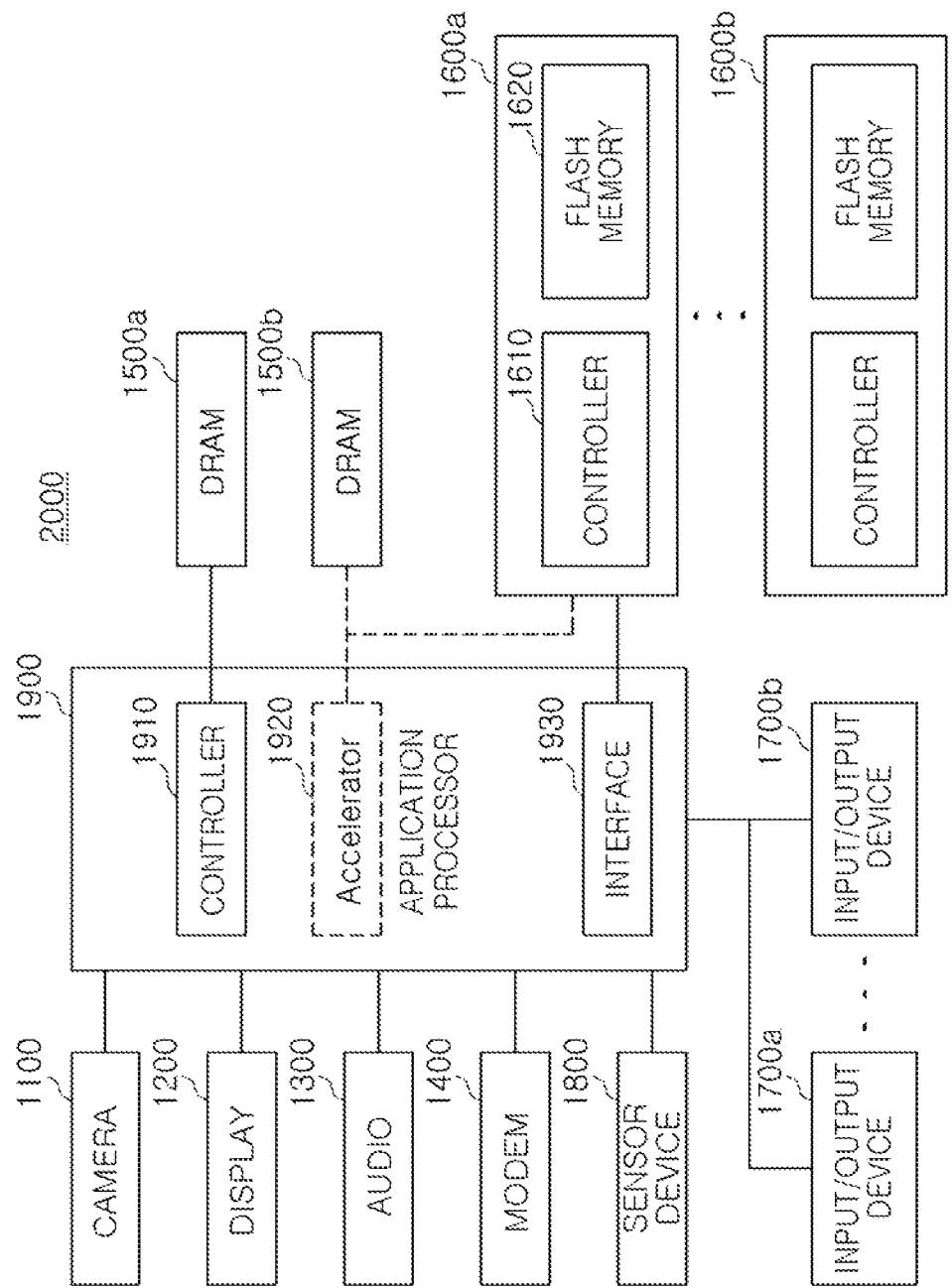
FIG. 18 is a schematic block diagram of a mobile device according to an example embodiment.

FIG. 18 is a schematic block diagram of a mobile device according to an example embodiment.

Referring to FIG. 18, a mobile device 1000 may include a camera 1100, a display 1200, an audio processing unit 1300, a modem 1400, DRAMs 1500a and 1500b, flash memory devices 1600a and 1600b, input/output (I/O) devices 1700a and 1700b, a sensor device 1800, and an application processor (hereinafter referred to as "AP") 1900.

The mobile device 1000 may be implemented as, e.g., a laptop computer, a portable terminal, a smartphone, a tablet personal computer (table PC), a wearable device, a healthcare device, or an Internet-of-Things (IoT) device. Also, the mobile device 1000 may be implemented as a server or a PC.

Various components included in the mobile device 1000 may operate in synchronization with a predetermined clock. For example, the display 1200 may display an image according to a predetermined scanning rate, and the DRAMs 1500a and 1500b and the flash memory devices 1600a and 1600b may store and read data at a predetermined speed or may operate according to a predetermined clock to exchange the data with external other devices. The I/O devices 1700a and 1700b and the application processor 1900 may also operate according to the predetermined clock.

The camera 1100 may capture a still image or a video under the user's control. The mobile device 1000 may obtain specific information using a still image/video captured by the camera 1100, or may convert and store the still image/video into other types of data such as text. The camera 1100 may include a plurality of cameras having different fields of view, stop values, or the like. The camera 1100 may further include a camera generating a depth image using depth information of a subject and/or a background, in addition to a camera imaging the subject to generate an actual image.

The display 1200 may provide a touchscreen function to be used as an input device of the mobile device 1000. In addition, the display 1200 may be integrated with a fingerprint sensor, or the like, to provide a security function of the mobile device 1000. The audio processing unit 1300 may process audio data, stored in the flash memory devices 1600a and 1600b, or audio data included in contents received from an external device through the modem 1400 or the I/O devices 1700a and 1700b.

The modem 1400 may modulate a signal and transmit the modulated signal to transmit and receive wired/wireless data, and may demodulate an externally received signal to restore an original signal. The I/O devices 1700a and 1700b may provide digital input and output, and may include an input device, such as a port connectable to an external recording medium, a touchscreen, or a mechanical button key, and an output device, capable of outputting a vibration in a haptic manner.

The sensor device 1800 may include a plurality of sensors collecting various types of external information. In an example embodiment, the sensor device 1800 may include an illuminance sensor detecting brightness of light, a gyro sensor detecting a movement of the mobile device 1000, a multi-channel optical sensor for obtaining biometric information from a user's body in contact with and/or proximate to the mobile device 1000, or the like. As an example, the multi-channel optical sensor may include a photoplethysmography (PPG) sensor and/or a spectrometer. The multi-channel optical sensor, included in the sensor device 1800, may include a light source, a sensor array, and a signal processing module processing a signal generated by the sensor array. As an example, the multi-channel optical sensor may be implemented according to the example embodiments described above with reference to FIGS. 3 to 14.

The AP 1900 may measure biometric information on a user's body, e.g., a pulse rate, a heart rate, blood oxygen saturation, a blood pressure, and the like, using data signals output by the multi-channel optical sensor, and may execute applications based on the biometric information.

The AP 1900 may control all operations of the mobile device 1000. For example, the AP 1900 may control the display 1200 to display a portion of the contents, stored in the flash memory devices 1600a and 1600b, on the screen. In addition, when receiving a user input through the I/O devices 1700a and 1700b, the AP 1900 may perform a control operation corresponding to the user input.

In an example embodiment, the AP 1900 may include an accelerator block 1920. According to another example embodiment, a separate accelerator chip may be provided separate from the AP 1900, and a DRAM 1500b may be additionally connected to the accelerator block 1920 or an accelerator chip. The accelerator block 1920 may be a functional block specialized in performing specific functions of the AP 1900, and may include a graphics processing unit (GPU) serving as a functional block specialized in processing graphics data, a neural processing unit (NPU) serving as a functional block specialized in performing AI computation and interference, a data processing unit (DPU) serving as a functional block specialized in transmitting data, or the like.

As described above, in an example embodiment, current signals output by a plurality of photodiodes may be encoded and then input to a single signal processing module, and a signal output by the signal processing module may be decoded to generate data signals corresponding to the current signals. Accordingly, noise reflected in a data signal in a process of converting the current signal into the data signal may be reduced to improve noise characteristics such as a signal-to-noise ratio (SNR).

As described above, example embodiments may provide a sensor device and a mobile device including the same which may improve noise characteristics. Example embodiments may encode current signals generated by a plurality of photodiodes, process the current signals by a single signal processing module, and decode an output of the signal processing module into data signals corresponding to the current signals.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A sensor device, comprising:
   a sensor array including a plurality of photodiodes configured to generate current signals in response to light;
   an encoder configured to encode the current signals to generate a plurality of analog signals, and output the plurality of analog signals sequentially;
   a signal processing module configured to process the analog signals, received from the encoder, to generate digital signals; and
   a decoder configured to decode the digital signals, received from the signal processing module, to generate a plurality of data signals corresponding to the current signals.

2. The sensor device as claimed in claim 1, wherein the data signals include biometric information to generate at least one of a heart rate, a blood oxygen saturation, and a blood pressure.

3. The sensor device as claimed in claim 1, wherein the sensor array is configured to generate the current signals in response to light reflected from a blood vessel in a human body.

4. The sensor device as claimed in claim 1, wherein:
   the encoder encodes the current signals based on a predetermined orthogonal code to generate the plurality of analog signals, and
   the decoder decodes the digital signals based on an inverse matrix of the orthogonal code to generate the plurality of data signals.

5. The sensor device as claimed in claim 4, wherein the number of the plurality of photodiodes is N (where N is a positive integer of 2 or more), and the orthogonal code is defined as an N-by-N matrix.

6. The sensor device as claimed in claim 1, wherein the encoder includes multipliers connected between the plurality of photodiodes and an input terminal of the signal processing module, and configured to multiply each of the analog signals by a predetermined coefficient.

7. The sensor device as claimed in claim 1, wherein:
   the signal processing module includes a positive input terminal and a negative input terminal, and
   the encoder includes a plurality of positive switches, connected between the plurality of photodiodes and the positive input terminal, and a plurality of negative switches connected between the plurality of photodiodes and the negative input terminal.

8. The sensor device as claimed in claim 7, wherein when the positive switch connected to one photodiode, among the plurality of photodiodes, is turned on, the negative switches connected to other photodiodes, among the plurality of photodiodes, are turned off.

9. The sensor device as claimed in claim 8, wherein the plurality of positive switches are sequentially turned on while the plurality of photodiodes output the analog signals.

10. The sensor device as claimed in claim 1, further comprising a light emitting unit configured to emit light, wherein:
a light emitting time, in which the light emitting unit is turned on, includes a plurality of unit times, and
the encoder multiplies at least some of the current signals by different coefficients in each of the plurality of unit times, and sums corresponding multiplication results to sequentially generate the analog signals.

11. The sensor device as claimed in claim 10, wherein each of the plurality of unit times has a duration corresponding to a time in which the signal processing module converts each of the analog signals into a digital domain.

12. A sensor device, comprising:
a plurality of photodiodes configured to generate current signals in response to light;
an encoder connected to the plurality of photodiodes through a plurality of analog channels, the encoder including a multiplier and an adder operating based on a predetermined orthogonal code, and configured to sequentially output a plurality of analog signals, obtained by encoding the current signals, to a single input channel;
a signal processing module including an input terminal connected to the input channel, and configured to successively output a plurality of digital signals corresponding to the analog signals, to an output terminal;
a decoder connected to the output terminal and configured to output a plurality of data signals, obtained by decoding the digital signals according to an inverse matrix of an orthogonal matrix corresponding to the orthogonal code, to a plurality of digital channels; and
a processor configured to generate information corresponding to the current signals using the data signals.

13. The sensor device as claimed in claim 12, wherein the encoder multiplies the current signals by encoding coefficients determined from the orthogonal code, and sums corresponding multiplication results to generate the analog signals.

14. The sensor device as claimed in claim 13, wherein each of the encoding coefficients is not zero.

15. The sensor device as claimed in claim 14, wherein, among the encoding coefficients for a respective current signal, one of the encoding coefficients is 1 and others of the encoding coefficients are −1.

16. The sensor device as claimed in claim 13, wherein the decoder multiplies the digital signals by decoding coefficients determined from the orthogonal code, and sums corresponding multiplication results to generate the data signals.

17. The sensor device as claimed in claim 16, wherein an absolute value of each of the decoding coefficients is smaller than an absolute value of each of the encoding coefficients.

18. The sensor device as claimed in claim 12, wherein the encoder includes a multiplier, connected to each of the analog channels, and an adder connected to the input channel.

19. The sensor device as claimed in claim 12, wherein the decoder includes an adder, a subtractor, and an accumulator connected to each of the digital channels.

20. A mobile device, comprising:
a substrate;
a plurality of photodiodes mounted on a first surface of the substrate and configured to generate current signals in response to light incident from an object;
a signal processing device mounted on the first surface or a second surface, facing the first surface, of the substrate and configured to convert the current signals into a plurality of data signals; and
a processor configured to obtain biometric information using the data signals,
wherein the signal processing device is configured to convert a plurality of analog signals, generated using the current signals received through a plurality of input channels, into a plurality of digital signals sequentially, and generate the data signals using the digital signals.

* * * * *